(12) United States Patent
Parrillo et al.

(10) Patent No.: US 6,897,175 B2
(45) Date of Patent: May 24, 2005

(54) CATALYST AND METHOD FOR THE ALKYLATION OF HYDROXYAROMATIC COMPOUNDS

(75) Inventors: David Parrillo, Schenectady, NY (US); Pramod Kumbhar, Bangalore (IN); Ashok Menon, Bangalore (IN); Mukund Parthasarathy, Delmar, NY (US); Geuch Zijlma, Goes (NL); Sunil Ashtekar, Bangalore (IN)

(73) Assignee: General Electric, Pittsfield, MA (US)

( * ) Notice: Subject to any disclaimer, the term of this patent is extended or adjusted under 35 U.S.C. 154(b) by 0 days.

(21) Appl. No.: 10/065,134

(22) Filed: Sep. 19, 2002

(65) Prior Publication Data

US 2003/0073572 A1 Apr. 17, 2003

Related U.S. Application Data

(60) Provisional application No. 60/327,802, filed on Oct. 9, 2001.

(51) Int. Cl.$^7$ ............................................. B01J 31/00
(52) U.S. Cl. ........................... 502/150; 156/89; 156/28; 501/80; 501/81; 501/82; 501/83
(58) Field of Search ........................... 502/150; 156/89, 156/28; 501/80, 81, 82, 83

(56) References Cited

U.S. PATENT DOCUMENTS

| | | |
|---|---|---|
| 3,306,874 A | 2/1967 | Hay |
| 3,306,875 A | 2/1967 | Hay |
| 3,446,856 A | 5/1969 | Hamilton, Jr. |
| 3,707,569 A | 12/1972 | van Sorge et al. |
| 3,764,630 A | 10/1973 | van Sorge |
| 3,790,641 A | 2/1974 | Oshima et al. |
| 3,843,606 A | 10/1974 | van Sorge |
| 3,873,628 A | 3/1975 | Van Sorge |
| 3,953,529 A | 4/1976 | Yonemitsu et al. |
| 3,962,181 A | 6/1976 | Sakauchi et al. |
| 3,968,172 A | 7/1976 | Ichikawa et al. |
| 3,972,828 A | 8/1976 | van Sorge |
| 3,972,836 A | 8/1976 | van Sorge |
| 3,974,229 A | 8/1976 | Van Sorge |
| 3,979,464 A | 9/1976 | Leach |
| 3,994,982 A | 11/1976 | Leach |
| 4,022,715 A | 5/1977 | Bornfriend |
| 4,022,843 A | 5/1977 | Leach |
| 4,024,195 A | 5/1977 | Yonemitsu et al. |
| 4,041,085 A | 8/1977 | Frabetti, Jr. |
| 4,048,239 A | 9/1977 | Smith |
| 4,083,828 A | 4/1978 | Olander |
| 4,085,150 A | 4/1978 | Smith |
| 4,092,294 A | 5/1978 | Bennett, Jr. et al. |
| 4,097,411 A | 6/1978 | van Sorge |
| 4,097,441 A | 6/1978 | Sircar et al. |
| 4,126,750 A | 11/1978 | Poe et al. |
| 4,128,728 A | 12/1978 | Arnold et al. |
| 4,140,773 A | 2/1979 | Stowell et al. |

(Continued)

FOREIGN PATENT DOCUMENTS

| | | |
|---|---|---|
| EP | 0102493 | 3/1984 |
| EP | 0 129 065 B1 | 5/1984 |
| EP | 0171792 | 2/1986 |
| EP | 0 438 329 A1 | 1/1991 |
| EP | 0 785 180 A2 | 1/1997 |
| EP | 0987220 A1 | 3/2000 |
| WO | WO 84/01146 | 3/1984 |
| WO | WO0138223 | 3/2001 |
| WO | WO 01/64334 A1 | 9/2001 |

OTHER PUBLICATIONS

International Search Report mailed Jan. 28, 2003.

Primary Examiner—Mark L. Bell
Assistant Examiner—Jennine M. Brown

(57) ABSTRACT

A metal oxide catalyst precursor composition comprises a pore former and a catalyst reagent.

32 Claims, 1 Drawing Sheet

U.S. PATENT DOCUMENTS

| | | |
|---|---|---|
| 4,165,439 A | 8/1979 | Smith |
| 4,179,411 A | 12/1979 | Broersma et al. |
| 4,201,880 A | 5/1980 | van Sorge |
| 4,208,537 A | 6/1980 | Kawamata et al. |
| 4,215,229 A | 7/1980 | Greco |
| 4,227,023 A | 10/1980 | Kawamata et al. |
| 4,227,024 A | 10/1980 | Leach |
| 4,269,735 A | 5/1981 | Leach |
| 4,283,574 A | 8/1981 | Leach |
| 4,290,924 A | 9/1981 | Leach |
| 4,322,566 A | 3/1982 | Leach |
| 4,329,517 A | 5/1982 | Taniguchi et al. |
| 4,351,958 A | 9/1982 | Takahata et al. |
| 4,361,709 A | 11/1982 | Kawamata et al. |
| 4,375,566 A | 3/1983 | Kawamata et al. |
| 4,386,226 A | 5/1983 | Adey et al. |
| 4,418,224 A | 11/1983 | Bennett et al. |
| 4,454,357 A | 6/1984 | Inoue et al. |
| 4,458,031 A | 7/1984 | Battista et al. |
| 4,460,702 A | 7/1984 | Smith |
| 4,469,908 A | 9/1984 | Burress |
| 4,471,149 A | 9/1984 | Adey et al. |
| 4,475,001 A | 10/1984 | Leston |
| 4,476,329 A | 10/1984 | Chambers et al. |
| 4,482,758 A | 11/1984 | Seig |
| 4,517,389 A | 5/1985 | Katsumata et al. |
| 4,528,407 A | 7/1985 | Smith et al. |
| 4,533,650 A | 8/1985 | Courty et al. |
| 4,547,480 A | 10/1985 | Bennett, Jr. et al. |
| 4,554,266 A | 11/1985 | Bennett et al. |
| 4,554,267 A | 11/1985 | Chambers et al. |
| 4,560,810 A | 12/1985 | Talley et al. |
| 4,572,778 A | 2/1986 | Ward |
| 4,590,307 A | 5/1986 | Bennett, Jr. et al. |
| 4,605,766 A | 8/1986 | Hargis |
| 4,644,086 A | 2/1987 | Voges et al. |
| 4,677,089 A | 6/1987 | Bennett, Jr. et al. |
| 4,720,478 A | 1/1988 | Voges et al. |
| 4,753,913 A | 6/1988 | Lenz et al. |
| 4,814,083 A | 3/1989 | Ford et al. |
| 4,822,836 A | 4/1989 | Wroczynski |
| 4,851,591 A | 7/1989 | Battista et al. |
| 4,874,810 A | 10/1989 | Lee, Jr. et al. |
| 4,876,398 A | 10/1989 | Lin et al. |
| 4,900,708 A | 2/1990 | Bennett et al. |
| 4,912,264 A | 3/1990 | Takeshita et al. ............ 568/790 |
| 4,933,509 A | 6/1990 | Warner |
| 4,954,475 A | 9/1990 | Bennett, Jr. et al. |
| 4,969,989 A | 11/1990 | Simpson |
| 5,017,655 A | 5/1991 | Kase et al. |
| 5,017,656 A | 5/1991 | Bopp |
| 5,059,727 A | 10/1991 | Ito |
| 5,097,079 A | 3/1992 | Bennett, Jr. et al. |
| 5,128,304 A | 7/1992 | Ito |
| 5,175,375 A | 12/1992 | Chang et al. |
| 5,227,342 A | 7/1993 | Anderson et al. |
| 5,245,089 A | 9/1993 | Irick, Jr. et al. |
| 5,321,105 A | 6/1994 | Rekers et al. ................ 526/104 |
| 5,345,005 A | 9/1994 | Thakur et al. |
| 5,371,306 A | 12/1994 | Woo et al. |
| 5,434,326 A * | 7/1995 | Gajda et al. ................. 585/467 |
| 5,488,173 A | 1/1996 | Wang |
| 5,563,106 A * | 10/1996 | Binner et al. .................. 501/84 |
| 5,622,684 A | 4/1997 | Pinnavaia et al. |
| 5,672,558 A | 9/1997 | White et al. |
| 5,795,559 A * | 8/1998 | Pinnavaia et al. .......... 423/702 |
| 5,840,271 A * | 11/1998 | Carrazza et al. ............ 423/700 |
| 5,847,237 A | 12/1998 | Yago et al. |
| 5,874,374 A * | 2/1999 | Ong ............................. 501/12 |
| 5,902,429 A * | 5/1999 | Apte et al. ............... 156/89.28 |
| 5,985,944 A * | 11/1999 | Ishizaki et al. ................ 521/64 |
| 5,986,138 A | 11/1999 | Satyavathi et al. |
| 5,998,317 A * | 12/1999 | Sterzel ........................ 501/80 |
| 6,024,899 A * | 2/2000 | Peng et al. ................. 264/29.1 |
| 6,037,295 A | 3/2000 | Satyavathi et al. |
| 6,042,763 A * | 3/2000 | Kumaoka .................... 264/44 |
| 6,049,008 A | 4/2000 | Roberts et al. |
| 6,054,627 A | 4/2000 | Thakur et al. |
| 6,153,547 A * | 11/2000 | Sterzel ........................ 501/80 |
| 6,187,981 B1 * | 2/2001 | Marinangeli et al. ........ 585/323 |
| 6,203,774 B1 | 3/2001 | Han et al. |
| 6,218,335 B1 * | 4/2001 | Okada et al. ............... 502/340 |
| 6,261,987 B1 | 7/2001 | Watson et al. |
| 6,291,724 B1 | 9/2001 | Braat |
| 6,294,499 B1 | 9/2001 | Watson et al. |
| 6,340,648 B1 * | 1/2002 | Imura et al. .................. 501/80 |
| 6,379,640 B1 * | 4/2002 | VerNooy ................. 423/239.1 |
| 6,395,674 B1 * | 5/2002 | Fung et al. ................. 502/214 |
| 6,395,871 B1 | 5/2002 | Watson et al. |
| 6,420,292 B1 * | 7/2002 | Kumaoka .................... 501/80 |
| 6,429,168 B1 * | 8/2002 | Vernooy ..................... 502/331 |
| 6,436,861 B1 * | 8/2002 | Suzuki et al. ................. 501/80 |
| 6,448,458 B1 * | 9/2002 | Marinangeli et al. ......... 585/24 |
| 6,455,748 B2 * | 9/2002 | Janssen et al. ............. 585/638 |
| 6,503,863 B2 * | 1/2003 | Fung et al. ................. 502/214 |
| 6,512,029 B1 * | 1/2003 | Gugumus ................... 524/97 |
| 6,541,407 B2 * | 4/2003 | Beall et al. ................. 501/119 |
| 6,541,415 B2 * | 4/2003 | Vaughn et al. ............. 502/214 |
| 6,620,751 B1 * | 9/2003 | Ogunwumi ................. 501/134 |
| 6,620,908 B2 | 9/2003 | Watson et al. |
| 6,642,164 B2 * | 11/2003 | Akaishi ........................ 501/80 |
| 6,649,802 B1 * | 11/2003 | Frame et al. ................ 585/533 |
| 6,657,022 B2 * | 12/2003 | Williams et al. .............. 526/72 |
| 6,667,261 B1 * | 12/2003 | Anshits et al. ................ 501/80 |
| 6,667,274 B1 * | 12/2003 | Hawley et al. ............. 502/415 |
| 6,743,747 B1 * | 6/2004 | Xu et al. .................... 502/214 |
| 2002/0128432 A1 | 9/2002 | Watson et al. |
| 2003/0073572 A1 | 4/2003 | Parrillo et al. |

* cited by examiner

CATALYST AND METHOD FOR THE ALKYLATION OF HYDROXYAROMATIC COMPOUNDS

CROSS REFERENCE TO RELATED APPLICATIONS

This application claims the benefit of the filing date of U.S. Provisional Application Ser. Nos. 60/327,802 filed Oct. 9, 2001, the entire contents of which is hereby incorporated by reference.

FEDERAL RESEARCH STATEMENT

Not Applicable

BACKGROUND OF INVENTION

This invention relates to alkylation catalysts and in particular to alkylation catalysts containing magnesium oxide or iron oxide, as well as combinations thereof and their methods of preparation. More particularly the invention relates to a method for preparing catalysts containing magnesium oxide or iron oxide for use in ortho-alkylation reactions of hydroxyaromatic compounds. The invention further relates to improvement in the process for the ortho-alkylation of hydroxyaromatic compounds using the above catalyst.

Ortho-alkylation reactions of hydroxyaromatic compounds typically involve vapor phase reaction of an hydroxyaromatic compound, e.g., phenol, with methanol using an alkylation catalyst. Such ortho-alkylated hydroxy aromatic compounds are well known for application as disinfectant, wood preservatives and even as a primary component in certain high-performance thermoplastic products.

U.S. Pat. Nos. 4,554,267; 4,201,880; 3,968,172 and 3,446,856 disclose the use of magnesium-based compounds such as magnesium oxide as a catalyst in the alkylation of the precursor hydroxyaromatic compound with a primary or secondary alcohol. Before the catalyst can be used in the alkylation reaction the catalyst needs to be subjected to calcination to convert the magnesium compound (e.g., magnesium carbonate or magnesium hydroxide) to magnesium oxide. The calcination is usually carried out at temperatures in the range of 350–500° C. Moreover, as discussed in U.S. Pat. No. 4,851,591 the calcination process may be carried out in suitable calcination atmosphere which can be oxidizing, inert, or reducing.

In such ortho-alkylation, it is very important for the catalyst to have high activity i.e. it must have as long and active a life as possible. Moreover, the catalyst should have very good ortho-selectivity. Many of the ortho-alkylation catalysts used are known to produce a mixture that often contains a high proportion of para-alkylated products and consequently such catalysts have marginal commercial utility.

It is known that selectivity and activity are related to the characteristics of the ortho-alkylation catalyst, and to the manner in which it is prepared. U.S. Pat. No. 4,554,267 (Chambers et al) discloses preparation of a magnesium-based catalyst from a slurry process using selected amounts of a copper salt as a promoter. In the process, the magnesium reagent and an aqueous solution of the copper salt are combined to form a magnesium-containing solid phase, which includes uniform, well-dispersed copper. The solid phase is dried, shaped, and calcined. The catalyst system is then used in the alkylation reaction of phenol and methanol. However, such slurry processes are associated with drawbacks such as in the "liquid"—related steps, which involve pre-blending of a copper compound with a magnesium compound and usually require mixing and holding tanks, recirculation piping, and specialized drying systems. Storage of the dried magnesium oxide/copper product (sometimes referred to as a "matrix") may also be required prior to blending and shaping steps. These steps and the huge investment in time and expense and are of limited commercial utility. Furthermore, the process suffers from unwanted contaminants into the catalyst which affect the desired activity/selectivity of the catalyst.

In addition to the aforementioned wet process, U.S. Pat. Nos. 6,261,987; 6,294,499 and 6,395,871 (Watson et al) describe the preparation of a magnesium-based catalyst using a dry blending method, preferably in the absence of a promoter. The catalyst is especially useful in the alkylation of phenol to manufacture 2,6-dimethyl phenol.

While it is evident from the above that alkylation of hydroxy aromatic compounds using metal oxide catalysts is in general well known and practiced in the art, a need continues to exist for methods and catalysts that have increased selectivity for ortho-alkylation to produce 2,6-dimethyl phenol (also referred to as 2,6-xylenol) with a reduction in the over-alkylation to produce 2,4,6-trimethyl phenol (mesitol). Over-alkylation to mesitol results in higher phenol and methanol usage thereby increasing the overall cost of production of 2,6-xylenol. Moreover, additional purification steps and expense are needed to remove the mesitol and provide a proper disposal method.

Thus, there exists an ongoing need for improvement in catalyst activity/selectivity for ortho-alkylation of hydroxy aromatic compounds so as to favor production of the desired alkylated compound substantially free of unwanted by-products thereby rendering such ortho-alkylation process more productive and cost-effective. As discussed above, the catalyst systems used in the alkylation reaction play an important role in such reactions and to bring about improvements in one or more of the following aspects: catalyst selectivity, catalyst activity, product yield, cost savings, and overall productivity.

SUMMARY OF INVENTION

A metal oxide catalyst precursor composition comprises a pore former (also referred to as a "pore modifier") and a catalyst reagent.

Another aspect is directed to improvement in the manufacture of alkylation catalysts by way of a heating and calcining method whereby the catalyst activity is improved while maintaining ortho-selectivity. In one embodiment, the catalyst precursor above is heated from ambient temperature to temperatures in the range of 350° C. to 600° C. followed by calcining at temperatures in the range of about 350° C. to about 600° C. under gas flow rate with weight hourly space velocity of between about 0.01 to 0.25. This gas can be selected from nitrogen, air and mixtures thereof.

In one embodiment, the improved method for preparing a metal oxide alkylation catalyst comprises the steps of (a) combining a pore former with at least one catalyst reagent selected from the group consisting of magnesium reagents and iron reagents to form a catalyst precursor composition and (b) calcining the catalyst precursor composition to form a metal oxide alkylation catalyst wherein the metal oxide alkylation catalyst has pores with a diameter between 100 and 400 Angstroms after calcination.

According to another embodiment, the invention relates to a method for alkylating a phenol species to produce an alkylated phenol species, wherein the method comprises alkylating the phenol in the presence of a metal oxide catalyst obtained as above and having pores with a diameter between 100 and 400 Angstroms.

DETAILED DESCRIPTION

Figure 1:
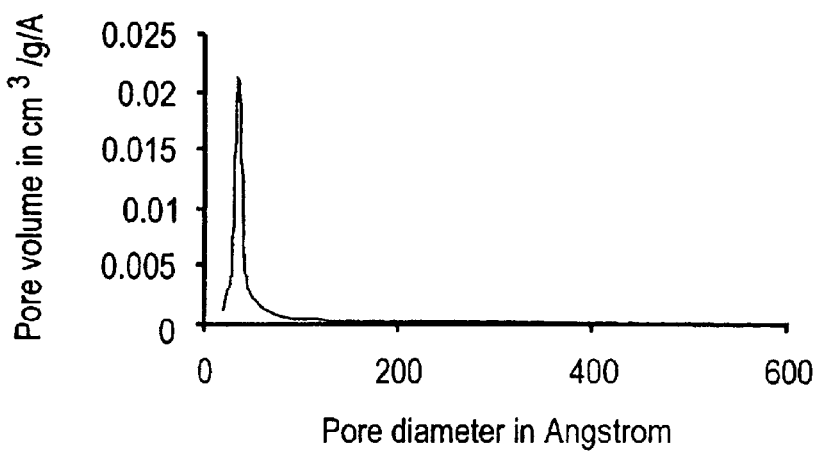
FIG. 1 illustrates the pore diameter distribution for a catalyst not containing a pore former.

It has been unexpectedly discovered that the pore size of the alkylating catalyst affects the product distribution such that increasing the pore size beyond what is typically obtained from calcination results in a reduction in the "over-alkylation" of phenol, i.e. a reduction in the amount of tri-alkylated phenol. Thus it is important to modify and tailor the catalyst morphology, in particular, to increase the pore size whereby the contact time between the alkylation catalyst and the hydroxyaromatic material would be reduced as compared to catalyst having a smaller pore size. Without being bound by theory, this reduction in contact time is believed to result in less over-alkylation, i.e. less mesitol being formed.

The catalysts described herein are those containing, as a main constituent, at least one metal oxide. The metal oxide can be obtained from a metal oxide precursor comprising at least one of a magnesium reagent or an iron reagent and mixtures containing at least one of the foregoing. Any magnesium reagent which yields magnesium oxide can be used. Likewise, any iron reagent which yields iron oxide can be used. The preferred magnesium reagents are magnesium oxide, magnesium hydroxide, magnesium carbonate, basic magnesium carbonate, and mixtures comprising any of any of the foregoing. The magnesium reagent is typically in the form of a powder. The average particle size for the powder is usually in the range of about 5 micrometers to about 50 micrometers.

Basic magnesium carbonate is especially preferred for many embodiments of this invention. As described in U.S. Pat. No. 4,554,267 basic magnesium carbonate is sometimes referred to as "magnesium carbonate hydroxide". It is identified in The Merck Index, Ninth Edition. It is also described in the Condensed Chemical Dictionary, Tenth Edition (1981), Van Nostrand Reinhold Company, page 633. Those skilled in the art understand that the exact formula for basic magnesium carbonate varies to some extent.

Magnesium reagents that are especially useful are selected from the group consisting of magnesium hydroxide, magnesium nitrate, magnesium carbonate, magnesium sulphate, magnesium acetate and mixture thereof.

Examples of iron reagents used for the preparation of the catalyst are ferric nitrate, ferric sulfate, ferric chloride, ferrous nitrate, ferrous sulfate and ferrous chloride. Of these, ferric nitrate is particularly preferred. Furthermore, the iron oxides can be in any form of $Fe_2O_3$, $Fe_3O_4$, or any mixtures thereof.

The pore former used in the catalyst precursor is basically a substance capable of aiding the formation of pores in the catalyst and is preferably selected from the group consisting of waxes and polysaccharides. The waxes can be selected from one or more of paraffin wax, polyethylene wax, microcrystalline wax, montan wax, and the like. The polysaccharide is selected from one or more of cellulose, carboxyl methyl cellulose, cellulose acetate, starch, walnut powder, citric acid, polyethylene glycol, oxalic acid, stearic acid and the like. Also useful are anionic and cationic surfactants, typically long chain ($C_{10-28}$) hydrocarbons containing neutralized acid species, e.g., carboxylic acid, phosphoric acid, and sulfonic acid species.

The amount of the pore former is that which provides for a distribution of pore diameters between 100 and 400 Angstroms pore size after calcination and typically ranges between about 100 ppm to 10 wt %, usually between about 100 ppm and 5 wt %, and preferably in amounts up to about 2 wt %, with respect to catalyst precursor reagent. The pore former is typically blended with the metal oxide precursor to provide uniform distribution of the pore former along with other components of the catalyst such as promoters, binders, and fillers.

The catalyst precursor of the invention involving the pore former is directed to the formation of a metal oxide alkylation catalyst that after calcination has a distribution of pores between about 100 Å to about 400 Å in diameter. Typically the metal oxide alkylation catalyst will have a bimodal distribution of pores. It is believed that the first and smaller diameter pore distribution is obtained from the metal oxide precursor during the calcination process, i.e. these pores are of similar dimension to those obtained from calcination of the metal oxide precursor not containing the pore former. The second and larger diameter pore distribution is believed to be the result of the addition and calcination of the pore former reagent itself, i.e. these pore diameters would not be found in substantial quantities after calcination of a metal oxide precursor not containing the pore former. Preferably, the bimodal distribution of pores has a first distribution of pores wherein the first distribution has an average pore diameter less than 100 angstroms and a second distribution of pores wherein the second distribution has an average diameter greater than 100 angstroms and less than 400 Angstroms.

In one embodiment, the process of manufacture of the metal oxide alkylation catalyst from the precursor material is directed to achieving higher activity while maintaining ortho selectivity of the catalyst by subjecting the precursor to a specific heating process prior to the actual calcination process. It was unexpectedly found that passing gas, e.g., nitrogen, air or a mixture thereof, through the catalyst during the initial heating step, during at least at substantial part of the calcination process step, and optionally during substantially all of the calcination process, resulted in improved performance of the calcined catalyst as compared to heating and calcining the catalyst without the gas flow or with an inert gas flow. It is believed that the gas aids in the formation of the desired pore size during the initial heating stage of the metal reagent containing the pore former. By carrying out the heating and calcination with a gas flow rate (weigh hourly space velocity or WHSV) of between about 0.01 to 0.25 using an nitrogen or an oxygen containing gas for at least a portion of the calcination temperature/time profile, it is possible to achieve higher activity and selectivity in ortho alkylation processes. A preferred WHSV is about 0.05 to about 0.15, although the actual flow rate will depend somewhat on the geometry of the catalyst. The gas used is preferably selected from oxygen, nitrogen, air and a mixture thereof.

Calcination is usually carried out by heating the catalyst at a temperature sufficient to convert the magnesium reagent or iron reagent to magnesium oxide or iron oxide, respectively. Useful calcination procedures are found in U.S. Pat. Nos. 6,294,499 and 4,554,267. The calcination temperature may vary somewhat, but is usually about 350° C. to about 600° C. Slow heating rates can lead to desirable larger pore sizes but often at the expense of lower activity of the resultant catalyst. Typically, the heating rate for commercial scale will be to raise the temperature from ambient to 400° C. over a 12 to 18 hour range although the exact rate can vary depending on the actual reactor size and geometry. The calcination atmosphere may be oxidizing, inert, or reducing. Alternatively, the catalyst can be calcined at the beginning of the alkylation reaction. In other words, calcination can take place in the presence of the alkylation feed materials, i.e., the hydroxy aromatic compound and the alkyl alcohol. The surface area of the catalyst after calcination is usually in the range of about 100 $m^2/g$ to about 250 $m^2/g$, based on grams of metal oxide.

The alkylation techniques are generally known in the art, and described in the above-referenced U.S. Pat. Nos. 4,554,267 and 3,446,856. Suitable processes are also described in U.S. Pat. Nos. 4,933,509; 4,900,708; 4,554,266; 4,547,480; 4,048,239; 4,041,085; and 3,974,229. A variety of alkylated compounds may be formed by this method; however, in many embodiments, 2,6-dimethylphenol is the preferred product. Usually, this material is produced by a gas phase reaction between phenol and methanol, utilizing the above described catalyst. Those skilled in the polymer- and chemical engineering arts are familiar with the details regarding this type of reaction. As the examples describe, use of the alkylation catalyst results in very good product formation rates, as well as excellent selectivity toward the desired alkylated product. Those familiar with chemistry and chemical reactions would be able to select the proper starting materials for each of the desired alkylated compounds.

An additional embodiment provides for an improved process of alkylating a phenol species to produce alkylated phenol species using the above discussed catalyst. The alkylated phenol species is preferably 2,6-dimethylphenol.

All references and patents cited are incorporated herein by reference.

The following examples are merely illustrative and should not be taken to be any sort of limitation on the scope of the claimed invention.

EXAMPLE I

Catalyst Preparation in Accordance with the Invention Using Magnesium Reagent 10 grams of magnesium carbonate was mixed with 1 gram of wax using a high speed sheer blender for 10 minutes. The blending process was carried out under liquid nitrogen in order to ensure homogeneous mixing. The resulting blend was calcined at 400° C. under continuous flow of air for 6 hours.

EXAMPLE II

Catalyst Preparation in Accordance with the Invention Using Magnesium Reagent 10 grams of magnesium carbonate was mixed with 5 grams of wax using a high speed sheer blender for 10 minutes. The blending process was carried out under liquid nitrogen in order to ensure homogeneous mixing. The resulting blend was calcined at 400° C. under continuous flow of air for 6 hours.

EXAMPLE III (Control)

Under this example the same process as that under Example I above was followed except that the catalyst precursor was simply magnesium carbonate precursor without the pore modifier.

Figure 2:
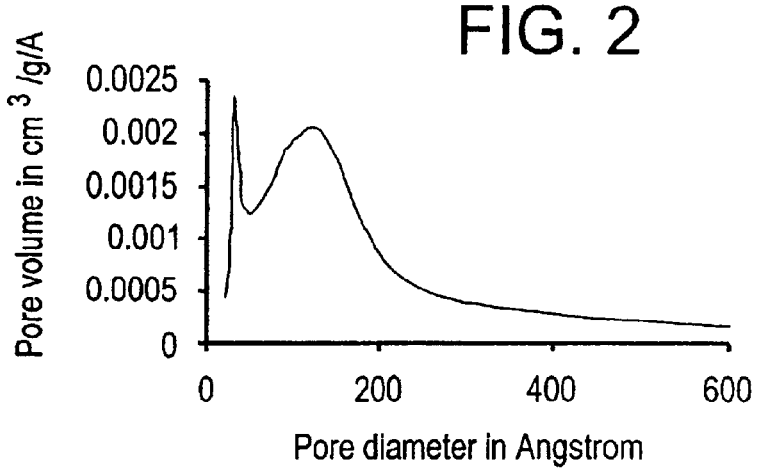
FIG. 2 illustrates the pore diameter distribution for a catalyst containing 10% by weight of a pore former versus the metal reagent highlighting the bi-modal nature of the distribution.
Figure 3:
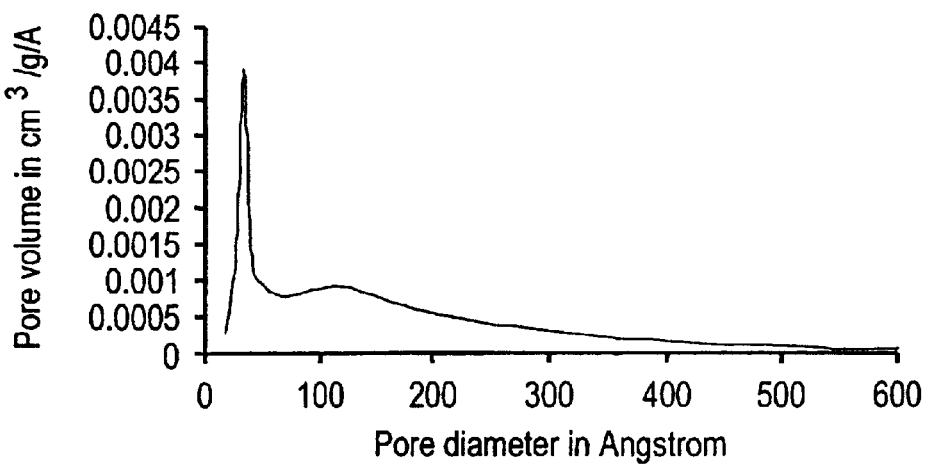
FIG. 3 illustrates the pore diameter distribution for a catalyst not containing 50% by weight of a pore former versus the metal reagent highlighting the bi-modal nature of the distribution.

Around 300 miligrams of calcined samples obtained following Examples I to III was subjected to surface area and porosity measurement using Micromeritics 2010 analyzer. The pore size distributions were obtained from the nitrogen desorption isotherm. The figures show pore size distribution of magnesium oxide obtained after treatment with 10 wt % of wax (Example I, FIG. 2) and 50 wt % of wax (Example II, FIG. 3) and magnesium oxide catalyst not containing an additional pore former (Example III, FIG. 1). The data demonstrate the bimodality developed by hydrocarbon wax treatment under Examples I & II and the large pore size obtained following the above process of the invention. A high proportion of larger pores with a diameter in the range of about 130 Å was obtained at low concentrations of wax.

EXAMPLE IV

Catalyst preparation in accordance with the invention using iron reagent. Iron oxide catalyst was obtained by room temperature precipitation from aqueous solution containing iron nitrate, chromium nitrate and sodium silicate with aqueous solution of ammonia (1:1) at pH=7. The precipitate was washed with water to remove nitrate ions and subsequently impregnated with potassium carbonate solution. This catalyst was dried at 120° C. followed by calcination at 470° C. under a continuous flow of nitrogen.

EXAMPLE V

Catalyst preparation in accordance with the invention using iron reagent. Iron oxide catalyst was obtained by refluxing an aqueous solution containing iron nitrate, chromium nitrate, sodium silicate, potassium carbonate with citric acid solution. The solution formed was evaporated using a rotavap, dried at 120° C. and subsequently calcined at 470° C. under a continuous flow of nitrogen.

EXAMPLE VI

Catalyst preparation in accordance with the invention using mixed iron/magnesium reagent. A mixed Iron oxide/Magnesium oxide catalyst was obtained by refluxing an aqueous suspension containing iron nitrate, magnesium carbonate, chromium nitrate, sodium silicate, potassium carbonate with citric acid. This suspension formed was evaporated using a rotavap, dried at 120° C. and subsequently calcined at 470° C. under a continuous flow of air.

Alkylation Examples

Procedure. A reactor was loaded with 100 cc of catalyst. The catalyst was calcined in situ for 22 hours at 380° C. under nitrogen, at atmospheric pressure. After calcination, the temperature was increased to 450° C. in two hours in a nitrogen atmosphere. After 15 minutes, a feed mixture was introduced at 4 cc/min, and reactor pressure was controlled to 25 psig. The feed contained 46.13 wt % methanol, 33.83 wt % phenol, and 20 wt % water (4:1 molar ratio of methanol to phenol). The alkylation was run for 165 hours at fixed conditions, during which the yields of o-cresol, 2,6-xylenol, p-cresol, 2,4-xylenol and mesitol were monitored. Illustrative data are found in Table 2 comparing a catalyst having a bi-modal pore distribution against a catalyst of the prior art. Conversion was measured at 165 hours, and is defined as the normalized wt % 2,6-xylenol in the effluent.

Conversion (%)=(Weight of 2,6-xylenol in effluent)×100/ (Weights of effluent phenolics) After 165 hours, the conditions were adjusted to achieve 65 wt % 2,6-xylenol in the effluent. At 165 hr, selectivity was calculated as: Selectivity= (Effluent moles (p-cresol+2,4-xylenol+mesitol))/(Effluent moles (phenol+o-cresol+2,6-xylenol)).

Sample 1 is a control experiment using a magnesium catalyst of the prior art prepared as described in U.S. Pat. No. 6,294,499 without a pore former.

Sample 2 is a experiment using a magnesium catalyst having a bimodal pore distribution with pore diameters centered at around 40 Angstroms and 100 to 150 Angstroms.

| | Catalyst | |
| --- | --- | --- |
| Description | Sample 1 no pore former | Sample 2 with pore former |
| 2,6 Xylenol conversion after 165 hrs (wt %) | 63–65 | 63–65 |
| Mesitol conversion after 165 hrs (wt %) | 3.6 | 1.9 |
| Para selectivity (%) | 3.7 | 2.4 |
| Excess Phenol usage (kg/100 kg 2,6 Xylenol) | 3.8 | 1.8 |

The data set forth above demonstrate the unexpected improved selectivity (indicated by the reduced percentage of mesitol) and reduced excess phenol usage that was obtained using a catalyst with bimodal pore distribution. Moreover, no significant loss in conversion was observed. Often, to obtain increased selectivity with a catalyst, an undesired reduction in conversion is obtained.

Polyphenylene ether resins were subsequently prepared from 2,6-xylenol products made using a catalyst having a bimodal pore distribution. These resins exhibited the same desirable attributes as those made in the prior art.

Having described preferred embodiments of the invention, alternative embodiments may become apparent to those skilled in the art without departing from the spirit of this invention and such equivalents/alternative embodiments are intended to be encompassed by the following claims.

What is claimed is:

1. A metal oxide alkylation catalyst precursor composition comprising a pore former and a catalyst reagent, wherein the pore former is present in an amount of between 0.01 and 10 percent by weight based upon the total weight of the catalyst reagent.

2. The catalyst precursor composition of claim 1 wherein the pore former is present in an amount of between 0.01 and 5 percent by weight based upon the total weight of the catalyst reagent.

3. The catalyst precursor composition of claim 1 wherein the catalyst reagent comprises a magnesium reagent, an iron reagent or a combination comprising one of the foregoing.

4. The catalyst precursor composition of claim 3, wherein the magnesium reagent comprises magnesium hydroxide, magnesium nitrate, magnesium carbonate, magnesium sulphate, magnesium acetate, or a combination comprising one of the foregoing.

5. The catalyst precursor composition of claim 3, wherein the iron reagent comprises ferric nitrate, ferric sulfate, ferric chloride, ferrous nitrate, ferrous sulfate, ferrous chloride, or a combination comprising one of the foregoing.

6. The catalyst precursor composition of claim 1, wherein the pore former is selected from the group consisting of waxes and polysaccharides.

7. The catalyst precursor composition of claim 6, wherein the pore former comprises paraffin wax, polyethylene wax, microcrystalline wax, montan wax, or a combination comprising one of the foregoing.

8. The catalyst precursor composition of claim 6, wherein the polysaceharide is selected from one or more of cellulose, carboxyl methyl cellulose, cellulose acetate, starch, and walnut powder.

9. The catalyst precursor composition of claim 1, wherein the pore former is selected from the group consisting of citric acid, polyethylene giycol, oxalic acid, and stearic acid.

10. The catalyst precursor composition of claim 1, wherein the pore former is selected from paraffin, polyethylene and mixtures thereof.

11. A catalyst made by calcining the catalyst precursor composition of claim 1 to produce a catalyst comprising pores.

12. The catalyst as claimed in claim 11, wherein the metal oxide alkylation catalyst has a bimodal distribution of pores less than 400 Angstroms.

13. The catalyst as claimed in claim 12, wherein the bimodal distribution of pores has a first distribution of pores wherein the first distribution has an average pore diameter less than 100 angstroms and a second distibution of pores wherein the second distribution has an average diameter greater than 100 angstroms and less than 400 Angstroms.

14. A method for preparing a metal oxide alkylation catalyst comprising the steps of (a) combining a pore former with at least one catalyst reagent selected from the group consisting of magnesium reagents and iron reagents to form a catalyst precursor composition and (b) calcining the catalyst precursor composition to form a metal oxide alkylation catalyst wherein the metal oxide alkylation catalyst has pores with a diameter between 100 and 400 Angstroms wherein step (a) the pore former is incorporated in an amount of between 0.01 and 10 percent by weight based upon the total weight of the catalyst reagent.

15. The method of claim 14, wherein in step (a) the pore former is incorporated in an amount of between 0.01 and 5 percent by weight based upon the total weight of the catalyst reagent.

16. The method of claim 14, wherein the catalyst reagent is selected from at least one of magnesium reagents and iron reagents.

17. The method of claim 14, wherein the magnesium reagent is selected from magnesium hydroxide, magnesium nitrate, magnesium carbonate, magnesium sulphate and magnesium acetate.

18. The method of claim 14, wherein the iron reagent is selected from ferric nitrate, ferric sulfate, ferric chloride, ferrous nitrate, ferrous sulfate and ferrous chloride.

19. The method of claim 14, wherein the pore former is selected from the group consisting of waxes and polysaccharides.

20. The method of claim 19, wherein the wax is selected from one or more of paraffin wax, polyethylene wax, microcrystalline wax, and montan wax.

21. The method of claim 19, wherein the polysaccharide is selected from one or more of cellulose, carboxyl methyl cellulose, cellulose acetate, starch, and walnut powder.

22. The method of claim 19, wherein the pore former is selected from one or more of citric acid, polyethylene glycol, oxalic acid, and stearic acid.

23. The method of claim 14, wherein the pore former is selected from paraffin, polyethylene and mixtures thereof.

24. The method of claim 14, wherein the pore former is present in an amount effective to result in pores having a diameter between 100 and 200 angstroms after the catalyst precursor composition has been subjected to calcination.

25. The method of claim 14, wherein the calcination is done under a flow of gas with a weight hourly space velocity of between about 0.01 to 0.25.

26. The method of claim 25, wherein the gas is selected from oxygen, nitrogen, air and mixtures thereof.

27. The method of claim 14, wherein the calcination is effected at a temperature between 350 and 600° C.

28. The method of claim 14, wherein the metal oxide alkylation catalyst has a bimodal distribution of pores less than 400Angstroms.

29. The method of claim 14, wherein the bimodal distribution of pores has a first distribution of pores wherein the first distribution has an average pore diameter less than 100 angstroms and a second distribution of pores wherein the second distribution has an average diameter greater than 100 angstroms and less than 400 Angstroms.

30. A metal oxide alkylation catalyst precursor composition comprising a pore former and a catalyst reagent, wherein the pore former is a wax or combination of waxes.

31. A metal oxide alkylation catalyst precursor composition consisting essentially of a pore former and a catalyst reagent, wherein the pore former is present in an amount of between 0.01 and 5 percent by weight based upon the total weight of the catalyst reagent.

32. A metal oxide alkylation catalyst precursor composition consisting of a pore former and a catalyst reagent wherein the pore former is present in an amount of between 0.01 and 10 percent by weight based upon the total weight of the catalyst reagent.

* * * * *